(12) United States Patent
Freedman

(10) Patent No.: US 7,053,611 B2
(45) Date of Patent: *May 30, 2006

(54) METHOD AND APPARATUS FOR USING PULSED FIELD GRADIENT NMR MEASUREMENTS TO DETERMINE FLUID PROPERTIES IN A FLUID SAMPLING WELL LOGGING TOOL

(75) Inventor: Robert Freedman, Houston, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 26 days.

This patent is subject to a terminal disclaimer.

(21) Appl. No.: 10/860,956

(22) Filed: Jun. 4, 2004

(65) Prior Publication Data
US 2005/0270023 A1  Dec. 8, 2005

(51) Int. Cl.
*G01V 3/00* (2006.01)

(52) U.S. Cl. ..................... 324/303; 324/300
(58) Field of Classification Search ............... 324/303, 324/300, 306, 309, 318
See application file for complete search history.

(56) References Cited

U.S. PATENT DOCUMENTS

| | | | |
|---|---|---|---|
| 5,291,137 A | 3/1994 | Freedman | |
| 5,428,291 A | 6/1995 | Thomann et al. | |
| 5,565,775 A | 10/1996 | Stallmach et al. | |
| 5,796,252 A * | 8/1998 | Kleinberg et al. | 324/303 |
| 6,107,796 A | 8/2000 | Prammer | |
| 6,111,408 A * | 8/2000 | Blades et al. | 324/303 |
| 6,229,308 B1 * | 5/2001 | Freedman | 324/303 |
| 6,346,813 B1 | 2/2002 | Kleinberg | |
| 6,350,986 B1 | 2/2002 | Mullins et al. | |
| 6,462,542 B1 | 10/2002 | Venkataramanan | |
| 6,570,382 B1 | 5/2003 | Hurliman et al. | |
| 6,737,864 B1 | 5/2004 | Prammer | |
| 6,856,132 B1 * | 2/2005 | Appel et al. | 324/303 |
| 6,937,014 B1 | 8/2005 | Sun et al. | |
| 2003/0128032 A1 | 7/2003 | Heaton et al. | |
| 2003/0169040 A1 | 9/2003 | Hurlimann et al. | |
| 2003/0214287 A1 | 11/2003 | Sun et al. | |

OTHER PUBLICATIONS

Stejskal et al., "Spin Diffusion Measurements: Spin Echoes in the Presence of a Time-Dependent Field Gradient," *J. Chemical Physics*, vol. 42, No. 1, pp. 288-292 (1965).

(Continued)

*Primary Examiner*—Brij B. Shrivastav
(74) *Attorney, Agent, or Firm*—Osha Liang; Kevin P. McEnaney; Bryan L. White

(57) ABSTRACT

A method for determining a formation fluid property includes acquiring a suite of nuclear magnetic resonance (NMR) measurements of a fluid sample using a pulse sequence that includes pulsed field gradient pulses for encoding diffusion information, wherein each NMR measurement in the suite is acquired with a different value in a parameter in the pulsed field gradient pulses for producing a different diffusion effect, wherein the acquiring is performed in a formation fluid sampling tool in a borehole; inverting the suite of NMR measurements to produce a distribution function that relates diffusion properties of the fluid sample with an NMR property of the fluid sample; and determining the formation fluid property from the distribution function.

17 Claims, 6 Drawing Sheets

OTHER PUBLICATIONS

Tanner, J., "Use of the Stimulated Echo in NMR Diffusion Studies," *J. Chemical Physics*, vol. 52, No. 5, pp. 2523-2526 (1970).

Karlicek et al., "A Modified Pulsed Gradient Technique for Measuring Diffusion in the Presence of Large Background Gradients," *J. Magnetic Resonance* 37, p. 75-91 (1980).

Cotts, et al., "Pulsed Field Gradient Simulated Echo Methods for Improved NMR Diffusion Measurements in Heterogeneous Systems," *J. Magnetic Resonance* 83, p. 252-266 (1989).

Kleinberg et al., "NMR Properties of Reservoir Fluids," *Log Analyst*, pp. 20-32 (Nov.-Dec. 1996).

Freedman et al., "A New NMR Method of Fluid Characterization in Reservoir Rocks: Experimental Confirmation and Simulation Results," *SPE Journal*, pp. 452-464 (Dec. 2001).

Lo, et al., "Mixing Rules and Correlations of NMR Relaxation Time with Viscosity, Diffusivity, and Gas/Oil Ratio of Methane/Hydrocarbon Mixtures," *SPE Journal*, p. 24-34, (Mar. 2002).

Fukushima et al., "Experimental Pulse NMR A Nuts and Bolts Approach," Addison-Wesley Publishing Co. Inc., Reading MA (1981).

Freedman et al., "Fluid Characterization using Nuclear Magnetic Resonance Logging," *Petrophysics* vol. 45, No. 3, pp. 241-251 (May-Jun. 2004).

Minh, et al., "Planning and Interpreting NMR Fluid-Characterization Logs," *SPE Journal 84478*, SPE Annual Technical Conference and Exhibition, Denver CO (Oct. 5-8, 2003).

\* cited by examiner

METHOD AND APPARATUS FOR USING PULSED FIELD GRADIENT NMR MEASUREMENTS TO DETERMINE FLUID PROPERTIES IN A FLUID SAMPLING WELL LOGGING TOOL

BACKGROUND OF INVENTION

1. Field of the Invention

This invention relates to methods and apparatus for determining formation fluid properties. More particularly, the invention relates to determination of the formation fluid properties using a downhole fluid sampling tool equipped with an NMR module.

2. Background Art

The oil and gas industry has developed various tools capable of determining formation fluid properties. For example, borehole fluid sampling and testing tools such as Schlumberger's Modular Formation Dynamics Testing (MDT™) Tool can provide important information on the type and properties of reservoir fluids in addition to providing measurements of reservoir pressure, permeability, and mobility. These tools may perform measurements of the fluid properties downhole, using sensor modules on board the tools. Alternatively, these tools can withdraw fluid samples from the reservoir that can be collected in bottles and brought to the surface for analysis. The collected samples are routinely sent to fluid properties laboratories for analysis of physical properties that include, among other things, oil viscosity, gas-oil ratio, mass density or API gravity, molecular composition, $H_2S$, asphaltenes, resins, and various other impurity concentrations. However, the laboratory data may not be useful or relevant to the reservoir fluid properties because the samples may have changed properties when brought to surface.

For example, the formation fluid may contain dissolved gas that will separate from liquids when the outside pressure drops. Similarly, the formation fluid may include substances that may precipitate out when the outside temperature drops. In either case, the measured laboratory data may not be relevant to the actual properties of the in situ reservoir fluids. Therefore, it is desirable that formation fluid analysis be performed under downhole conditions.

Several U.S. Patents disclose methods and apparatus for making NMR measurements in a borehole on fluid samples withdrawn from earth formations. For example, U.S. Pat. No. 6,346,813 B1 issued to Kleinberg (the '813 patent) discloses an NMR module on the flowline of the MDT™ tool for determining different fluid properties from magnetic resonance signals. The '813 patent is assigned to the assignee of the present invention and is hereby incorporated by reference in its entirety. U.S. Pat. No. 6,107,796 issued to M. Prammer discloses apparatus and methods for determining the level of contamination in a formation crude oil sample that may be contaminated by oil-based mud filtrate. The method discloses in this patent monitors changes in NMR responses of fluid samples as a function of time while the fluid samples are pumped from the formation into a sampling tool.

Formation fluids often contain several components, each of which likely has a different diffusion property. Therefore, measurement of diffusion coefficients may provide valuable information on the formation fluid properties. Some NMR methods make use of magnetic field gradients to probe the diffusion properties of the formation fluids. For example, U.S. Pat. No. 6,737,864 issued to Prammer et al. discloses an apparatus for making T1 measurements on fluids flowing in the flowline of a fluid sampling tool. This application also discloses a static gradient method for making diffusion measurements on stationary samples. The method of deriving the diffusion data from the NMR measurements assumes a single diffusion constant. However, it is well known that crude oils have a distribution of diffusion coefficients. Thus, it is desirable to have methods that can provide diffusion coefficients of formation fluids without assuming that they have the same diffusion constants.

U.S. Pat. No. 6,111,408 (the '408 patent) issued to Blades et al. discloses methods and apparatus for measuring the relaxation times (T1 and T2) and the diffusion coefficients (D) of fluids in an NMR module of a fluid sampling tool. A method disclosed in this patent uses an electromagnet to generate an oscillating pulse field gradient (PFG) in between refocusing pulses of CPMG pulse sequence. The oscillating PFG is phased locked (synchronized) with the CPMG pulses (see FIG. 5 in the '408 patent). The pulse field gradient de-phases the spins and then is turned off for a period, during which the spins diffuse. Following the diffusion period, the oscillating pulse field gradient is turned on to re-phase the spins followed by a spin-echo. The first spin-echo is then re-focused by a train of radio frequency 180-degree pulses to obtain more spin-echoes. While the phase-locked oscillating PFG pulses are capable of providing diffusion encoding, better methods and apparatus for accomplishing diffusion encoding are desirable.

U.S. Pat. No. 6,346,813 B1 issued to Kleinberg discloses an NMR module for characterizing fluids in a fluid sampling and testing tool, such as the MDT™ tool. This patent discloses methods for relating relaxation times and diffusion coefficients of fluids to viscosity, gas-oil ratio (GOR), and other fluid properties of interest. A related U.S. Pat. No. 5,796,252 issued to Kleinberg et al. (the '252 patent) discloses the use of PFG-CPMG sequence to encode diffusion information. A simple approximation method is then used to obtain a diffusion coefficient from the PFG-CPMG data. The diffusion coefficient is then used to correct for spin echo magnitudes in order to derive more accurate oil volumes in reservoirs. The methods disclosed in the '252 patent also assume a single diffusion coefficient for crude oils.

U.S. Pat. No. 6,462,542 B1 issued to L. Venkataramanan et al. (the '542 patent) discloses "diffusion-editing" pulse sequences. The diffusion information is encoded using a static gradient of the applied magnetic field using a wireline or logging-while-drilling (LWD) NMR logging tool. These pulse sequences are modifications of CPMG sequences. The pulse sequence differs from the CPMG sequence in that one or a few of the early echoes are acquired with a long echo spacing in order to produce diffusion attenuation of the echoes. The remaining echoes are acquired with a short spacing to minimize diffusion effects (D). The '542 patent also discloses an inversion of a physics model using a suite of diffusion-editing pulse sequences that provides 2-dimensional distribution functions of D–T2, T1–T2, and T1/T2–T2.

U.S. Pat. No. 6,570,382 by Hürlimann et al. also discloses "diffusion editing" pulses sequences that may include a pulsed field gradient sequence.

While various NMR apparatus and methods are available for determining formation fluid properties, better methods and apparatus for determining formation fluid properties are still needed.

SUMMARY OF INVENTION

One aspect of the invention relates to methods for determining a formation fluid property. A method in accordance with one embodiment of the invention includes acquiring a suite of nuclear magnetic resonance (NMR) measurements of a fluid sample using a pulse sequence that includes pulsed field gradient pulses for encoding diffusion information, wherein each NMR measurement in the suite is acquired with a different value in a parameter in the pulsed field gradient pulses for producing a different diffusion effect, wherein the acquiring is performed in a formation fluid sampling tool in a borehole; inverting the suite of NMR measurements to produce a distribution function that relates diffusion properties of the fluid sample with an NMR property of the fluid sample; and determining the formation fluid property from the distribution function.

Another aspect of the invention relates to an NMR sensor. An NMR sensor in accordance with one embodiment of the invention includes a permanent magnet capable of generating a substantially homogeneous magnetic field across a sample chamber; a radiofrequency antenna surrounding the sample chamber, wherein the radiofrequency antenna is configured to generate oscillating magnetic fields that have magnetic moments substantially orthogonal to a direction of the substantially homogeneous magnetic field generated by the permanent magnet; and at least one coil connected to a control unit, wherein the at least one coil and the control unit are configured to generate pulsed magnetic field gradient across the sample chamber in a controlled manner such that the pulsed magnetic field gradient has a selected strength and a predetermine duration.

Other aspects of the invention would become apparent from the following description, the drawings, and the claims.

DETAILED DESCRIPTION

Embodiments of the invention relate to apparatus and methods for determining reservoir fluid properties using an NMR module in a downhole tool, such as a fluid sampling tool disclosed in U.S. Pat. No. 6,346,813 B1 issued to Kleinberg. An example of formation fluid tester tool is the Modular Formation Dynamics Testing tool sold under the trade name of MDT™ by Schlumberger Technology Corp. (Houston, Tex.).

Figure 1:
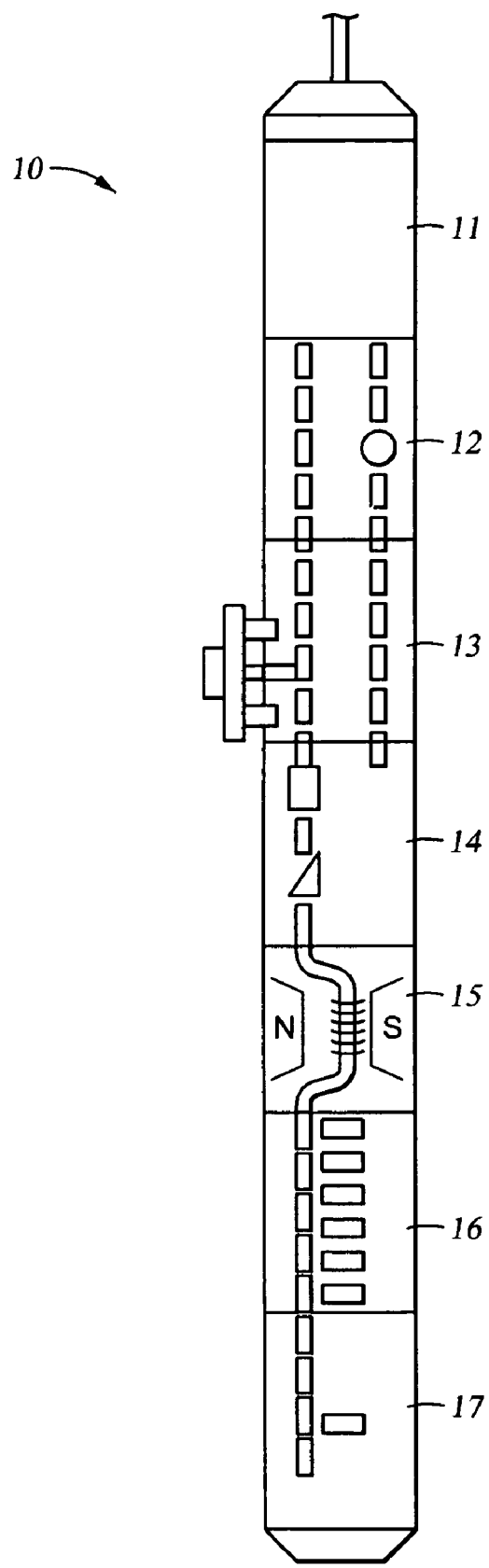
FIG. 1 shows a prior art formation fluid testing (sampling) tool having an NMR module.

FIG. 1 shows an exemplary formation fluid testing (or sampling) tool 10 (e.g., an MDT™ tool) that includes the following modules: an electronic module 11, which may include a processor and a memory; a hydraulic power module 12; a probe module 13, which may be deployed to make a hydraulic seal with the formation; a pumpout module 17; an optical fluid analyzer (OFA) 14; and a multisample module 16. In addition, the formation fluid sampling tool 10 includes an NMR module 15. The NMR module 15 may include an NMR sensor of the invention.

An NMR sensor in accordance with embodiments of the invention includes a permanent magnetic that can produce a substantially homogeneous static magnetic field over the volume of the fluid sample. In addition, the NMR sensor includes at least one coil that can produce pulsed field gradients (PFG) of defined strengths and durations across the sample volume. A homogeneous static magnetic field in combination with a pulsed magnetic field gradient can provide measurements with better signal-to-noise ratios because a larger sample volume is resonated, as compared to a static magnetic field having a static field gradient, which can only induce a small portion of the sample (a "sample slice") to resonate. The NMR sensor of the invention also includes a coil (an RF antenna) for producing radio frequency (RF) magnetic field pulses. The magnetic moment of the RF antenna is substantially perpendicular to the magnetic moment of the static magnetic field.

Figure 2:
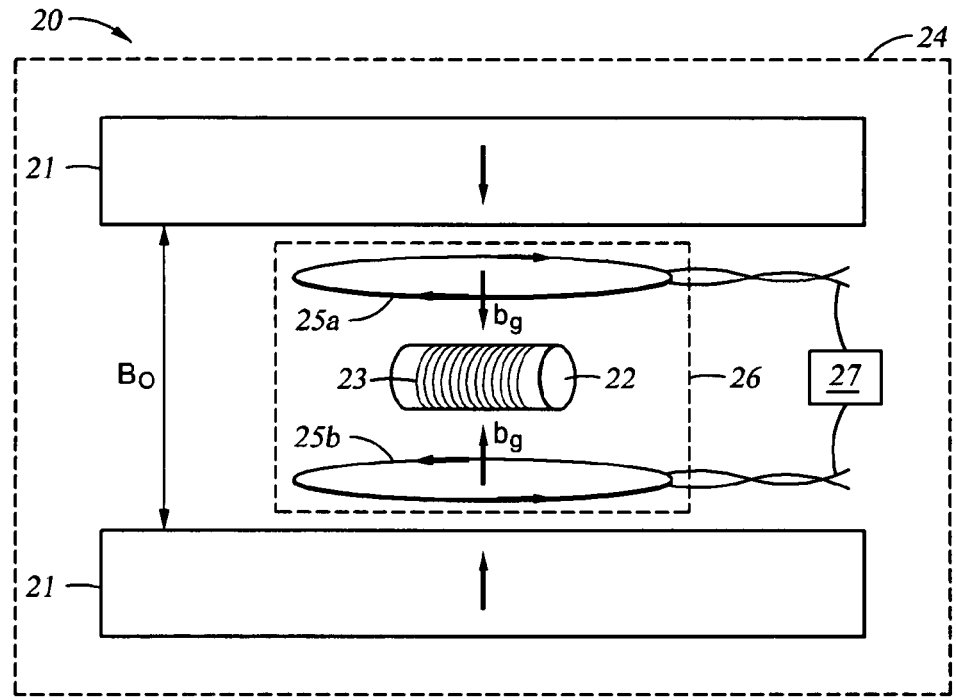
FIG. 2 shows an NMR sensor in accordance with one embodiment of the invention.

FIG. 2 shows an NMR sensor in accordance with one embodiment of the invention. As shown in FIG. 2, an NMR sensor 20 includes a magnet 21 (e.g., a permanent magnet) that is designed to produce a substantially homogeneous magnetic field ($B_0$) in a sample volume 22. The permanent magnet 21 may be made of Samarium Cobalt or any other suitable material. The permanent magnet 21, which may comprise a single piece or several pieces that surround the sample volume 22, may further include permeable pole pieces attached to its surfaces for shaping the magnetic field and for reducing the magnetic field gradient in the sample region so that the static field is substantially homogeneous over the sample volume (sample chamber) 22.

In some embodiments, the sample volume 22 may be configured to connect in a formation fluid flow line so that the sensor 20 may be used to measure or monitor the fluid properties flowing through the sample volume (sample chamber) 22. An RF antenna (coil) 23 surrounds the sample volume 22. The RF antenna 23 is designed to radiate an oscillating radiofrequency (RF) magnetic field ($B_1$) having a magnetic moment substantially perpendicular (orthogonal) to that of the static magnetic field produced by the permanent magnet 21. The RF antenna 23 may comprise a solenoid coil, a saddle coil, or any other suitable coil. One of ordinary skill in the art would appreciate that the same RF antenna 23 may function as a transmitter to transmit the oscillating magnetic field and as a receiver to receive the signals, as disclosed in U.S. Pat. No. 6,346,813 B1 issued to Kleinberg. Alternatively, separate transmitter and receiving antennas may be used.

The NMR sensor 20 shown in FIG. 2 also includes two gradient coils 25a and 25b that are configured to produce magnetic field gradients across the volume of the sample 22. The gradient coils 25a and 25b are connected to a control unit 27 that can energize the gradient coils 25a and 25b at a selected strength for a predetermined duration. While two gradient coils 25a and 25b are shown, one of ordinary skill in the art would appreciate that one or more gradient coils may be used without departing from the scope of the invention. During the duration of a gradient pulse, opposing magnetic fields $b_g$ may be created to induce a magnetic field gradient g over the sample volume. The magnetic field gradient g is usually measured in units of Gauss/cm. The sensor 20 may be protected and supported by a casing 24. The casing 24 may be made of a a magnetic steel with high magnetic permeability for the confining the magnetic field $B_0$ and for providing strength to the assembly.

In addition, some embodiments of the invention may include a shield 26 that separates the RF antenna 23 and the permanent magnet 21. The shield may be made of a material (e.g., copper) that can prevent the oscillating RF magnetic field produced by the RF antenna 23 from interacting with the permanent magnet 21 so that magneto-acoustic ringing in the magnet can be minimized.

An NMR sensor in accordance with embodiments of the invention may be used to make measurements related to the diffusion and relaxation properties of fluid samples. Because these properties are generally different for oil and water, these measurements can provide a means for determining the relative proportion of water and oil in a fluid sample. In addition, these measurements can provide information on the properties of the oils, including their compositions, viscosities and gas/oil ratios (amounts of solution gas contained in the oil). Similarly, for a fluid sample, which may comprise (1) gas and water, (2) gas, oil, and water, (3) oil and gas, or (4) oil and water, the measurements can provide a means for determining the relative proportions of the different components that are present. In addition, these measurements can provide information on the hydrocarbon properties that are important for determining the monetary value of the reservoir and also essential for making well completion decisions.

Figure 3:
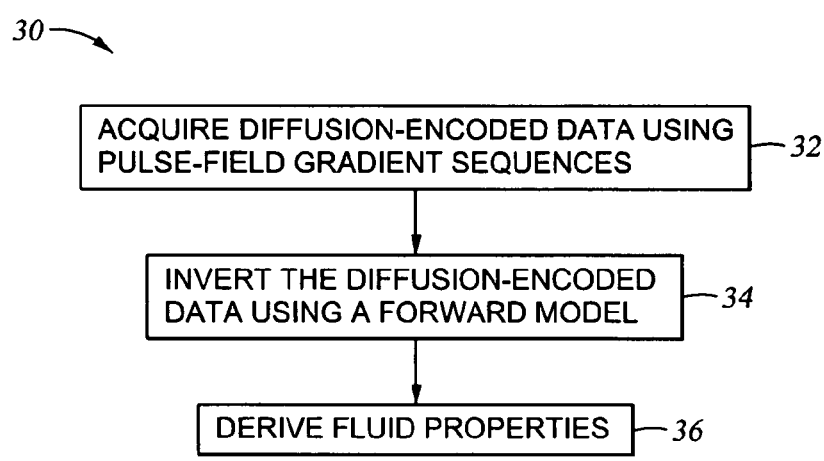
FIG. 3 shows a method for determining formation fluid properties in accordance with one embodiment of the invention.

FIG. 3 shows a method in accordance with one embodiment of the invention. As shown in FIG. 3, the method 30 includes the step of acquiring a suite of diffusion-encoded NMR data (step 32). The diffusion encoding is achieved using pulsed-field gradient pulses in each acquisition. One of the parameters in the PFG pulses is varied for each measurement in the suite of data such that each measurement includes a different diffusion effect. Next, the diffusion-encoded data are inverted according to a forward model, i.e., a physics model describing the decay of the spin-echo signals (step 34). The inversion produces a distribution function related to fluid properties, for example, a two-dimensional (2-D) distribution function, $f(D,T_2)$, that correlates the diffusion (D) coefficients with the spin-spin (T2) relaxation times. Finally, the desired fluid properties (e.g., diffusion coefficients, viscosities, molecular composition, etc.) may be extracted from the distribution function (step 36). These steps are described in more detail in the following sections.

NMR pulsed field gradient measurement is a standard technique for measuring the diffusion coefficients of molecules in liquids and solids. The most widely used technique for liquids is the Stejskal and Tanner method (The Journal of Chemical Physics, v. 42, no. 1, 288–292, 1965), which is referred to as the PFG method. The PFG method can be used to accurately measure diffusion coefficients as small as $\approx 10^{-8}$ cm²/s. For viscous liquids and solids with slower diffusion and/or fast transverse relaxation, a stimulated-echo pulsed field gradient (SEPFG) developed by Tanner (The Journal of Chemical Physics, Vol. 52, No. 5, pp. 2523–2526, 1970) is widely used. The SEPFG methods provide better results than the PFG methods only if the spin-lattice relaxation times $(T_1)$ are appreciably longer than the transverse or spin-spin $(T_2)$ relaxation times. Both PFG and SEPFG sequences use pulsed field gradients to encode diffusion information in the spin-echo measurements.

A method of the invention may use a PFG or an SEPFG pulse sequence. The physical basis underlying both techniques is that the Brownian motion of the molecules causes an attenuation of the NMR signal magnitudes that can be related to the diffusion coefficients of the molecular constituents in the sample. The additional 180-degree pulses are used to re-focus the first echo and are added for the purpose of acquiring information on the other mechanism of signal decay, i.e., $T_2$ decay of the spin echoes. In the following description, these sequences will be referred to as the PFG-CPMG (i.e., Stejskal and Tanner pulsed field gradient sequence followed by a train of 180-degree pulses) and SEPFG-CPMG (i.e., Tanner stimulated echo pulse field gradient sequence followed by a train of 180-degree pulses).

Figure 4:
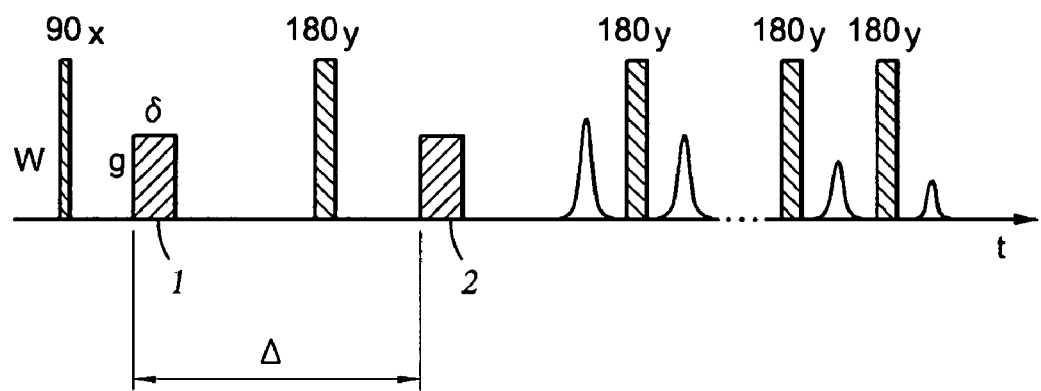
FIG. 4 shows a PFG-CPMG pulse sequence in accordance with one embodiment of the invention.

FIG. 4 shows a diagram illustrating a PFG-CPMG pulse sequence in accordance with one embodiment of the invention. As shown, two pulsed field gradient (PFG) pulses 1 and 2 are inserted after the first 90° pulse and the first 180° pulse, respectively, in a typical PFG pulse sequence. The first echo is then re-focused by application of a train of 180° pulses. The PFG pulses are separated by a delay time Δ and each has a field gradient strength g and a duration δ. The delay time Δ, field gradient strength g, and the duration δ each can be varied to produce a different diffusion effect.

A method in accordance with embodiments of the invention for determining reservoir fluid properties involves acquisition of a suite of PFG-CPMG or SEPFG-CPMG measurements. The number of measurements in each suite depends on many factors. In general, about 10 or few measurements in a suite may be sufficient. Each measurement in the suite differs from each other by having a different amount of diffusion attenuation of the echoes due to the change of one or more pulse parameters in the PFG-CPMG or SEPFG-CPMG sequences. As noted above and shown in FIG. 4, these parameters include the duration of the pulsed gradient (δ), strength of the pulsed gradient (g), separation (delay) of the gradient pulses (Δ) in the PFG sequence.

The NMR measurements thus obtained are "diffusion-encoded" and can be inverted to produce a distribution function, relating to fluid properties. For example, the distribution function may be a two-dimensional (2-D) distribution function, $f(D,T_2)$, relating diffusion (D) coefficients to the spin-spin (T2) relaxation times of the sample. For an oil-water sample, the 2-D $f(D,T_2)$ distribution can be used to estimate, among other things, the relative volumes of the oil and water, oil viscosity, molecular composition of the oil, and gas-oil ratio.

Furthermore, one-dimensional (1-D) distributions of diffusion and relaxation times for the oil and the water can be separately computed from the 2-D distribution. In addition, suites of partially polarized PFG-CPMG sequences can be acquired and inverted to produce a 3-dimensional distribution function $f(D,T_2,T_1)$ that includes the spin-lattice relaxation time $(T_1)$ or a $T_1/T_2$ ratio.

The suite of pulsed field gradient data can be inverted based on a physics model (a forward model) that describes the decay of the spin-echo signals to obtain (in general) the three-dimensional diffusion and relaxation time distribution function, $f(D,T_2,T_1)$, for the fluid sample. If there is a sufficient recovery or wait time prior to each measurement in the data suite; then there is no $T_1$ dependence and the inversion produces a two-dimensional distribution function, ƒ(D,T$_2$). These distribution functions provide valuable information on the properties of the fluid samples.

Description of Pulse Sequences, Sensor, and Forward Model

Referring again to FIG. 4, the PFG-CPMG pulse sequence includes a 90° excitation pulse produced by an RF magnetic field (B$_1$) along the x-axis in the reference frame rotating about B$_0$ at the average Larmor frequency ($\omega_L$). The 90° pulse rotates the magnetization vector into the transverse (i.e., x-y) plane. A magnetic field gradient (g) of duration ($\delta$) is then applied, which causes a position dependent dephasing of the spins. After a short delay, a 180° pulse is applied to change the signs of the phases of the spins (or the sense of rotation of the spins in the transverse plans). After another short delay, a second gradient pulse is applied to re-phase the spins which have been de-phased by the first gradient pulse. The re-phasing is effective only if the spins have not diffused away from their initial locations. For those spins that have diffused to a new location during the diffusion time ($\Delta$), re-phasing will not be perfect. The imperfect re-phasing caused by diffusion of the spins leads to diffusion attenuation of the echo. Information on the spin-spin relaxation time (T$_2$) is provided by further application of a series of 180° pulses that generate a train of spin-echoes. The general expression, for a homogeneous static magnetic field, for the transverse magnetization (M(t)) measured by the pulse sequence shown in FIG. 4 is given by the following equation, $$M(t) = \int \int \int f(D, T_1, T_2) \cdot \exp(-t/T_2) \cdot \left(1 - \exp\left(-\frac{W}{T_1}\right)\right) \cdot \quad (1)$$
$$\exp(-(\gamma \cdot g \cdot \delta)^2 D(\Delta - \delta/3)) dD dT_1 dT_2,$$

where M(t) is evaluated at times t at which the spin-echoes in FIG. 4 occur.

Eq. 1 is a Fredholm integral equation of the first kind that is satisfied by a 3-D distribution function of diffusion coefficients and relaxation times, ƒ(D, T$_1$, T$_2$). The exponential factor in the integrand that contains T$_2$ accounts for the spin-spin relaxation of the magnetization, while the factor that contains T$_1$ accounts for the incomplete polarization of the magnetization if starting from an initial state of zero magnetization. A recovery time W precedes the first 90° pulse shown in FIG. 4. If the wait time W is sufficiently long (e.g., say 5 times the longest T$_1$ in the sample), then the incomplete polarization factor is equal to one. In this case, the 3-D distribution function reduces to the 2-D distribution function, ƒ(D, T$_2$).

The exponential factor that contains the pulsed field gradient parameters, as derived by Stejskal and Tanner (1965), accounts for the attenuation of the echoes caused by diffusion. The pulsed field gradient attenuation factor in Eq. 1 would be more complicated, if there is a static gradient (g$_s$) in addition to the pulsed field gradient. In this case, Stejskal and Tanner show that the attenuation factor caused by diffusion in Eq. 1 contains two additional terms: a cross term g.g$_s$ and a second term that is proportional to the square of the static gradient, i.e., g$_s$.g$_s$. The preferred embodiments of this invention use a static magnet field that is substantially homogeneous over the sample volume so that the complications arising from static field gradients can be avoided. However, those skilled in the art would appreciate that modifications of the Stejskal and Tanner pulsed field gradient sequences are available that can reduce the effects of the static gradient. Using such modified pulse field gradient sequences, embodiments of the invention may be practiced in the presence of static gradients. Suitable sequences can include, but are not limited to, the pulsed field gradient sequences disclosed by Karlicek and Lowe ("*A Modified Pulsed Gradient Technique for Measuring Diffusion in the Presence of Large Background Gradients*" in J. of Mag. Res., v 37, p. 75–91, 1980) and Cotts, et al. ("*Pulsed Field Gradient Simulated Echo Methods for Improved NMR Diffusion Measurements in Heterogeneous Systems*" in J. of Mag. Res., v. 83, p. 252–266, 1989).

For measuring diffusion in viscous liquids and solids Tanner (J. of Chemical Physics, v. 52, no. 5, 2523–2526) developed an alternative to the Stejskal and Tanner sequence known as a "stimulated echo pulse field gradient" (SEPFG) sequence. This sequence can provide for more robust measurement that can detect very small diffusion coefficients and is optimal in systems for which T$_1$>>T$_2$. A Tanner stimulated echo sequence, coupled with a CPMG sequence, is shown in FIG. 5.

Figure 5:
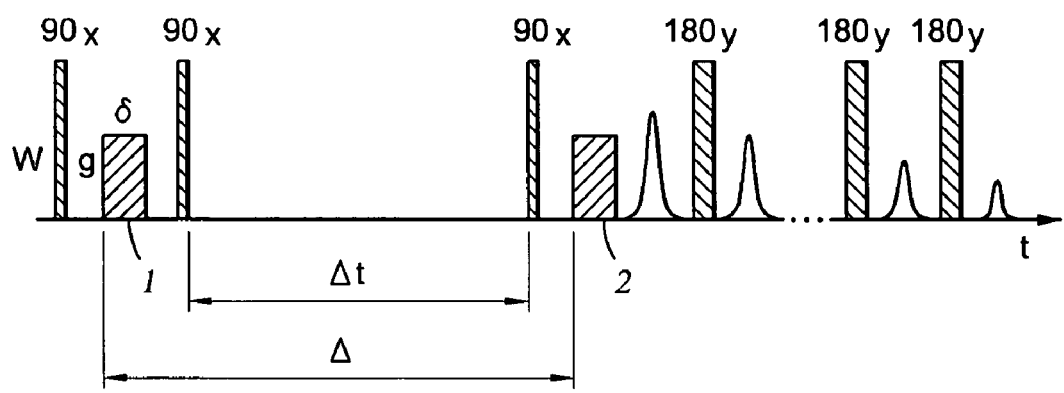
FIG. 5 shows a SEPFG-CPMG pulse sequence in accordance with one embodiment of the invention.

As shown in FIG. 5, a pair of 90° pulses are inserted between the two PFG pulses. In this sequence, the second 90° pulse rotates the magnetization into the z-direction (along the direction of the static field), where it undergoes longitudinal (T$_1$) relaxation during the time interval ($\Delta\tau$) between the second and third 90° pulses. However, in practice, only about one-half of the randomly oriented spins, i.e., those that are projected along the y-axis in the rotating frame, are rotated into the z-direction by the second 90° pulse. As a result, there is a loss of about 50% of the signals in the stimulated echo method. The storage of the magnetization in the z-direction during the interval between the second and the third 90° pulses allows for a longer diffusion time ($\Delta$) to measure small diffusion coefficients. This technique circumvents the strong attenuation of the signals that would otherwise result from fast T$_2$ relaxations, e.g., in very viscous liquids or solids, if the Tanner and Stejskal sequence is used.

Neglecting static gradients the magnetization for the SEPFG-CPMG pulse sequence obeys the equation, $$M(t) = \int \int \int f(D, T_1, T_2) \cdot \exp(-t/T_2) \cdot \left(1 - \exp\left(-\frac{W}{T_1}\right)\right) \cdot \quad (2)$$
$$\exp\left(-\Delta\tau\left(\frac{1}{T_1} - \frac{1}{T_2}\right)\right)\{\exp(-(\gamma \cdot g \cdot \delta)^2 D(\Delta - \delta/3)) dD dT_1 dT_2\}.$$

Eq. 2 differs from Eq. 1 in that it has an additional exponential factor in the integrand. This factor, which contains the difference of the inverses of T$_1$ and T$_2$, accounts for the fact that there is longitudinal relaxation but no transverse relaxation in the interval ($\Delta\tau$) between the second and third 90° pulses in FIG. 5. The parameter, $\Delta\tau$, is the time the magnetization is stored in the longitudinal direction, i.e., the time difference between the third and second 90° pulses.

Similar to the case with the Stejskal and Tanner (PFG) sequence, the presence of a static magnetic field gradient (g$_s$) would complicate the diffusion attenuation of the stimulated echo (SEPFG) sequence. In the presence of a static magnetic field gradient (g$_s$), there is a cross term g.g$_s$ plus a second term proportional to the square of the static gradient g$_s$.g$_s$. The coefficients of the additional terms are described in Tanner (1970, Eq. 7), which also shows that the pulsed field gradient induced attenuation caused by diffusion has an identical form to that in Eq. 1. Thus, the magnetization in the SEPFG-CPMG sequence shown in FIG. 5 encodes the diffusion effects in a manner similar to the PFG-CPMG sequence. Therefore, in the absence of static gradients, the diffusion attenuation term in Eq. 2 is identical to the one in Eq. 1. Preferred embodiments of the invention use a magnet that produces an essentially homogeneous field to simplify data analysis. However, if static field gradient exists, those skilled in the art would appreciate that the effects of the static gradient terms can be reduced or eliminated by using a modified stimulated pulse field gradient sequence (see e.g., Cotts, et al. "*Pulsed Field Gradient Simulated Echo Methods for Improved NMR Diffusion Measurements in Heterogeneous Systems*" in J. of Mag. Res., v. 83, p. 252–266, 1989).

Figure 6:
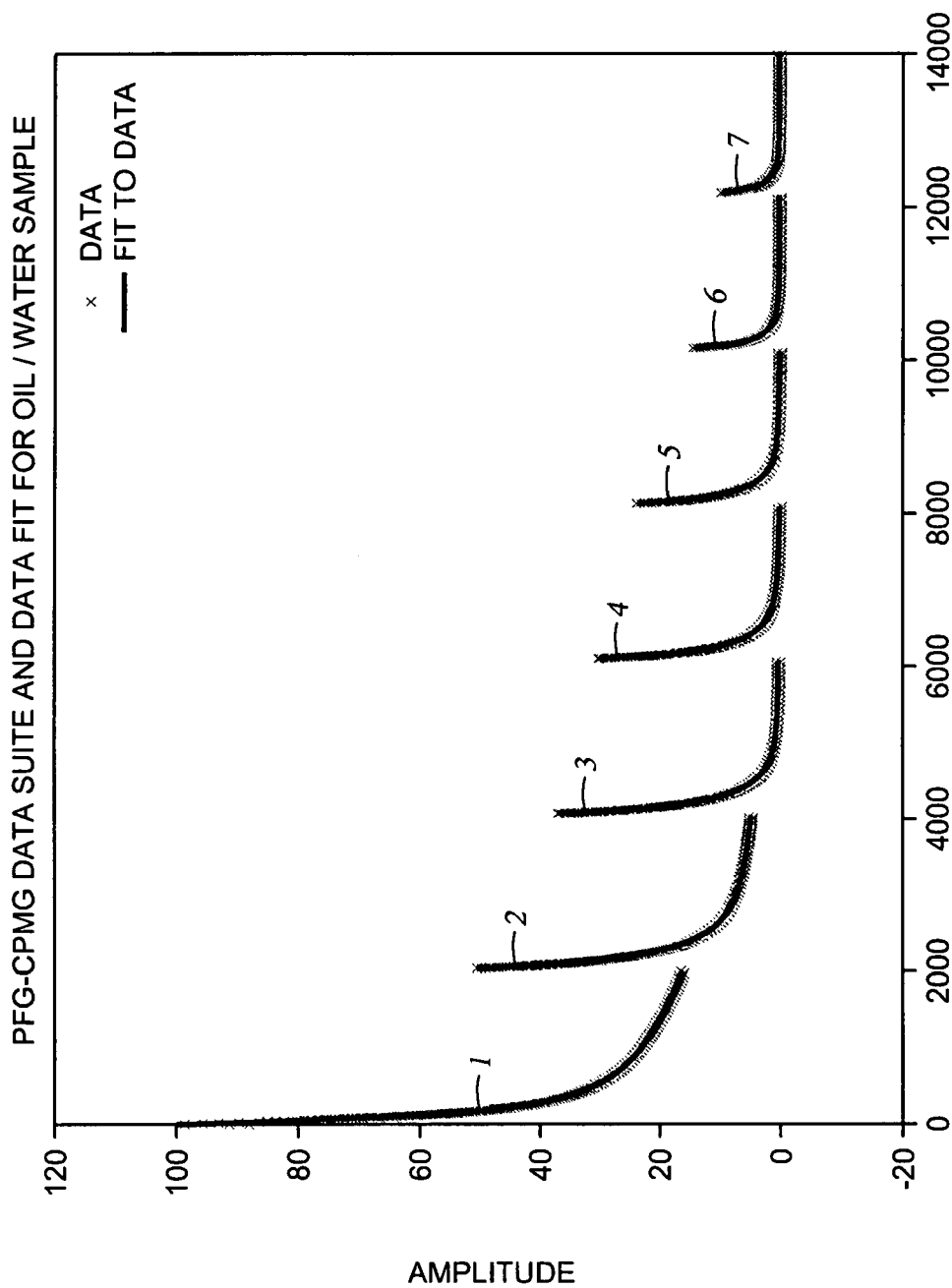
FIG. 6 shows a suite of PFG-CPMG diffusion-encoded data that can be used to determine a formation fluid property using a method in accordance with one embodiment of the invention.

The following example illustrates the utility of a method of the invention. FIG. 6 shows a suite of NMR data that are obtained with the pulse parameters shown in Table 1.

TABLE 1

PFG Pulse Parameters Used for the Suite of PFG-CPMG Data Shown in FIG. 6

| Measurement | δ (s) | Δ (s) | g (Gauss/cm) |
|---|---|---|---|
| 1 | NA | NA | NA |
| 2 | 0.002 | 0.02 | 30.0 |
| 3 | 0.004 | 0.02 | 30.0 |
| 4 | 0.006 | 0.02 | 30.0 |
| 5 | 0.008 | 0.02 | 30.0 |
| 6 | 0.012 | 0.02 | 30.0 |
| 7 | 0.015 | 0.02 | 30.0 |

The data suite shown in FIG. 6 consists of a standard CPMG with 5000 echoes and a 0.2 ms echo spacing (trace 1) and 6 Stejskal and Tanner PFG-CPMG sequences each having 5000 echoes (traces 2–7). The second and subsequent echoes (traces 2–7) in the PFG-CPMG sequences also have 0.2 ms spacings. For these data, there is no $T_1$ dependence because the sequences were all fully polarized. In this case, the 3-D distribution function reduces to a 2-D function of diffusion (D) and spin-spin relaxation time (T2), as shown FIG. 7.

As noted above, the diffusion information in a suite of pulsed field gradient sequences can be coded into the data by variation of one or more of the three pulse parameters in the diffusion attenuation term in Eqs. 1–2. For the data suite shown in FIG. 6, which is used to compute the 2-D distribution function in FIG. 7, the parameter δ was varied for each of the 6 PFG-CPMG sequences in the suite (traces 2–7). The other two diffusion attenuation pulse parameters, Δ and g, were held constant.

In this example, the first measurement is obtained with a standard CPMG sequence (i.e., without PFG). Note that it is not necessary to include a standard CPMG measurement in a PFG-CPMG data suite. In fact, the inclusion of a standard CPMG measurement may result in artifacts in the 2D distribution function because the standard CPMG measurement does not provide any diffusion information.

The computation of distribution functions from a data suite requires inversion of a forward model specified by Eq. 1 for a PFG-CPMG data suite or by Eq. 2 for an SEPFG-CPMG data suite. These equations are known as Fredholm integral equations of the first kind, the inversion of which may be accomplished by various methods as discussed voluminously in publications, patents, and books. For example, U.S. Pat. No. 5,291,137 issued to Freedman discloses a "window processing" inversion method that may be used for this purpose. This patent is incorporated by reference in its entirety.

The following describes the process of computing a distribution function (e.g., FIG. 7) from a suite of data as shown in FIG. 6. The forward model in Eq. 1 for the magnetization measured by a PFG-CPMG sequence can be simplified, without loss of generality, by using a suite of fully polarized measurements, i.e., $W \gg T_1$, for which the polarization function can be set equal to 1. Then, integration over $T_1$ reduces the 3-D distribution function to a 2-D function of diffusion (D) and spin-spin relaxation time ($T_2$).

The use of a suite of fully-polarized data provides a more straightforward illustration of how a method of the invention works. However, methods of the invention are not limited to suites of fully polarized data. In fact, the computation of a 3-D distribution function using a partially polarized suite of data presents not much more difficulty and can be handled in the same manner as described below. Similarly, the solution of Eq. 2 using suites of SEPFG-CPMG data may be obtained by the same method. Thus, the computation can be illustrated with the following equation, $$M(t) = \int\int f(D, T_2) \cdot \exp(-t/T_2) \cdot \exp(-(\gamma \cdot g \cdot \delta)^2 D \cdot (\Delta - \delta/3)) \, dD dT_2, \quad (3)$$

or in a discrete version suitable for numerical solution, $$M_j = \sum_{l,k} f_{l,k} \exp\left(-\frac{t_j}{T_{2,l}}\right) \exp(-(\gamma \cdot g \cdot \delta)^2 D_k (\Delta - \delta/3)). \quad (4)$$

where the index j=1, 2, 3, . . . , NE denotes the j-th echo and NE is the total number of echoes acquired in the PFG-CPMG sequence. The relaxation times $T_{2,l}$ with l=1, 2, 3, . . . , N are a set of N fixed relaxation times that span the range of expected $T_2$ values. It is convenient, but not essential, for the fixed relaxation times to be selected equally spaced on a logarithmic scale. Similarly, the $D_k$ is a set of N fixed diffusion coefficients selected to span the range of expected D values. The N by N matrix, $f_{l,k}$, is the discrete representation of the continuous 2-D diffusion and relaxation time distribution function. The echoes occur at times, $$t_j = te_1 + (j-1) \cdot te, \quad (5)$$

where $te_1$ is the time at which the first echo occurs, i.e., $te_1 = 2\tau$, where $\tau$ is the time between the 90° pulse and the first 180° pulse in FIG. 4; and te is the spacing between the second and subsequent echoes. The measured echo amplitudes are then related to the forward model in Eq. 4 by the equation, $$\tilde{M}_j^p = M_j^p + J_j^p. \quad (6)$$

where the index p=1, 2, 3, . . . , P is used to indicate a particular measurement in a suite of P measurements. Note that the index p is also used to label the pulse parameters used in a particular PFG-CPMG sequence (e.g., the parameters are $\delta_p$, $g_p$, and $\Delta_p$).

Equation 6 indicates that the measured phase corrected echo amplitudes ($\tilde{M}_j^p$) include those given by the forward model ($M_j^p$) and a term that accounts for random thermal noises ($J_j^p$). The measured echo amplitudes are typically recorded using two-channel quadrature detection. The measured two-channel amplitudes are phase-corrected and the noise power ($\Psi_p$) for each measurement may then be computed using the methods disclosed in U.S. Pat. Nos. 5,291,137 and 6,229,308 B1 both issued to Freedman. These two patents are incorporated in their entireties by reference. The inversion of Eq. 1 may be performed by the methods disclosed in these two patents. For example, a set of window sums $\tilde{I}_m^p$ are computed from the phase-corrected spin-echo amplitudes, i.e., from the equation, $$\tilde{I}_m^p = \sum_{j=N_m^p+\rho_m}^{N_{m+1}^p} \tilde{M}_j^p \equiv I_m^p + J_m^p. \tag{7}$$

where $I_m^p$ is the sum of the forward model (i.e., theoretical, noise-free echo amplitudes) over a set of pre-determined windows and can be written in the form, $$I_m^p = \sum_{l=1}^{N} \sum_{k=1}^{N} f_{l,k} F_m^p(T_{2,l}) \exp(-(\gamma \cdot g_p \cdot \delta_p)^2 D_k (\Delta_p - \delta_p/3)). \tag{8}$$

In the above equations, the index m=1, 2, ..., $n_w^p$, where $n_w^p$ is the number of window sums for the measurement in the data suite having index p=1, 2, ..., $N_{meas}$, where $N_{meas}$ is the number of measurements in the data suite. The quantities $N_m^p$ and $N_{m+1}^p$ in Eq. 7 are the left and right endpoints (echo numbers), respectively, of the m-th window for the p-th measurement; $\rho_m$ is defined to follow the convention, introduced in U.S. Pat. No. 5,291,137, that only the first window contains its left endpoint and it is defined by the relation, $$\rho_m = 1 - \delta_{m,1} \tag{9}$$

where $\delta_{m,l}$ is the well-known Kronecker delta function. Therefore, $\rho_1=0$ and $\rho_m=1$ when m is not equal to 1. In Eq. 8 the sensitivity functions $F_m^p(T_{2,l})$ are defined by the equation, $$F_m^p(T_{2,l}) = \sum_{j=N_m^p+\rho_m}^{N_{m+1}^p} \exp\left(-\frac{t_j^p}{T_{2,l}}\right). \tag{10}$$

where $t_j^p$ is the time at which the j-th echo occurs for measurement p in the data suite. As shown in U.S. Pat. No. 5,291,137, the variance of the noise summed over the m-th window is given by the variance in the noise per echo multiplied by the number of echoes in the window for uncorrelated noise. This is expressed by the equations, $$\langle (J_m^p)^2 \rangle = \hat{\sigma}_{m,p}^2 \Psi_p, \tag{11}$$

where, $\hat{\sigma}_{m,p}^2 = N_{m+1}^p - N_m^p + \delta_{m,1}$ is the number of echoes in the m-th window for the p-th measurement in the data suite.

The diffusion and relaxation time matrix can be computed, subject to a positivity constraint, by minimizing, with respect to $f_{l,k}$ in Eq. 8, a cost function (or another objective function) of the form, $$F\{f_{l,k}\} = \sum_p \sum_m \frac{(\tilde{I}_m^p - I_m^p)^2}{2\Psi_p \hat{\sigma}_{m,p}} + \alpha \sum_l \sum_k f_{l,k}^2. \tag{12}$$

Minimization of Eq. 12 with respect to the amplitudes in the diffusion and relaxation time distribution matrix provides a solution of the inverse problem by fitting the measured window sums to the theoretical values. The term containing the parameter $\alpha$ is known as a "squared norm" regularization and is added for the purpose of selecting physically sensible and stable solutions from the infinity of possible solutions. The parameter $\alpha$ can either be fixed or computed from the data. The minimization of cost functions of the form shown in Eq. 12 is described in detail in U.S. Pat. No. 6,229,308 B1 and will not be repeated here for the sake of brevity.

Figure 7:
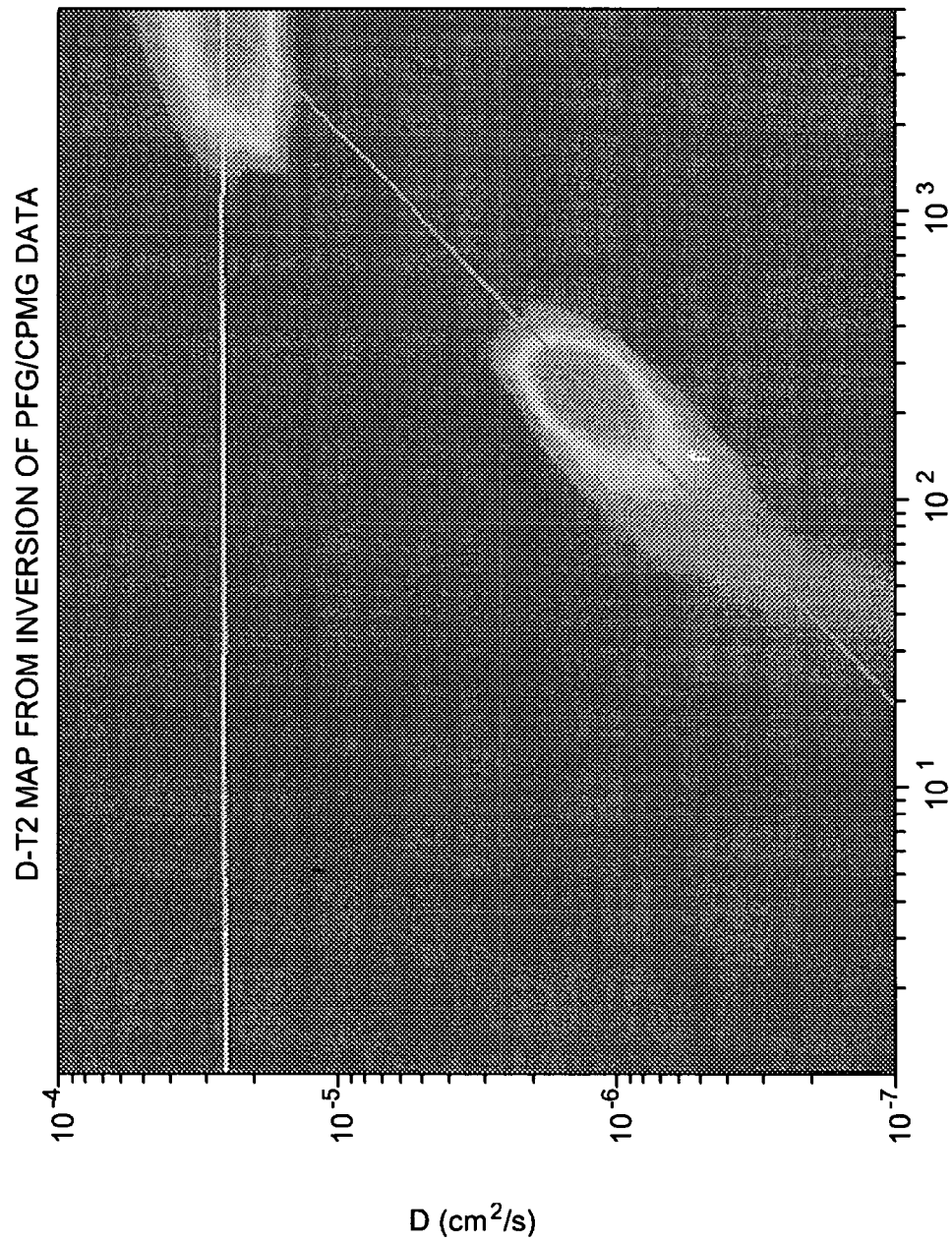
FIG. 7 shows a plot of a 2D distribution function computed from the suite of data shown in FIG. 6 in accordance with one embodiment of the invention.

Plotting the matrix $f_{l,k}$ that resulted from the minimization of Eq. 12 produces a 2-D distribution of diffusion and relaxation time, as shown in FIG. 7. The data suite used for this inversion is the suite of PFG-CPMG data shown in FIG. 6 for a fluid sample containing 70% of an intermediate viscosity crude oil and 30% water. The plot of the 2-D distribution function shown in FIG. 7 may be produced with any commercially available software, such as Matlab™ available from Mathworks Corporation (Natick, Mass.). As shown in FIG. 7, the 2-D distribution function, as computed with a method of the invention, accurately predicts two components. The peak centered around D=$2.5 \times 10^{-5}$ cm$^2$/s and T2=$5 \times 10^3$ ms is that of water, and that centered around D=$1 \times 10^{-6}$ cm$^2$/s and T2=260 ms is that of the oil.

Once the distribution function is computed, the calculated distribution function ($f_{l,k}$) in Eq. 1 may be used to compute the theoretically predicted spin-echo amplitudes for each measurement in the data suite. The computed data suite can then be compared with the data shown in FIG. 6. Any deviations of the theoretical echo amplitudes from the measured values may be used to compute a "chi-squared" or goodness of fit parameter that is useful for assessing the quality of the solution. It will be appreciated by those skilled in the art that the analysis presented above can be readily extended to the computation of 3-D distribution functions.

One-Dimensional Relaxation Time and Diffusion Coefficient Distributions

One-dimensional relaxation time and diffusion coefficients can be computed from the 2-D or 3-D distributions by integrating over the other variables. For example, the 1-D distribution function of relaxation times can be computed from the integral, $$f(T_2) = \int f(T_2, D) dD. \tag{13}$$

Note that the above equations use a transparent notation for the distribution functions, in which the number and kind of arguments are used to indicate the dimensionality and type of distribution. Using the discrete form of the 2-D distribution function in Eq. 4, the discrete relaxation time distribution function may be computed by summation, i.e., $$f(T_{2,l}) = \sum_{k=1}^{N} f_{l,k}. \tag{14}$$

Figure 8:
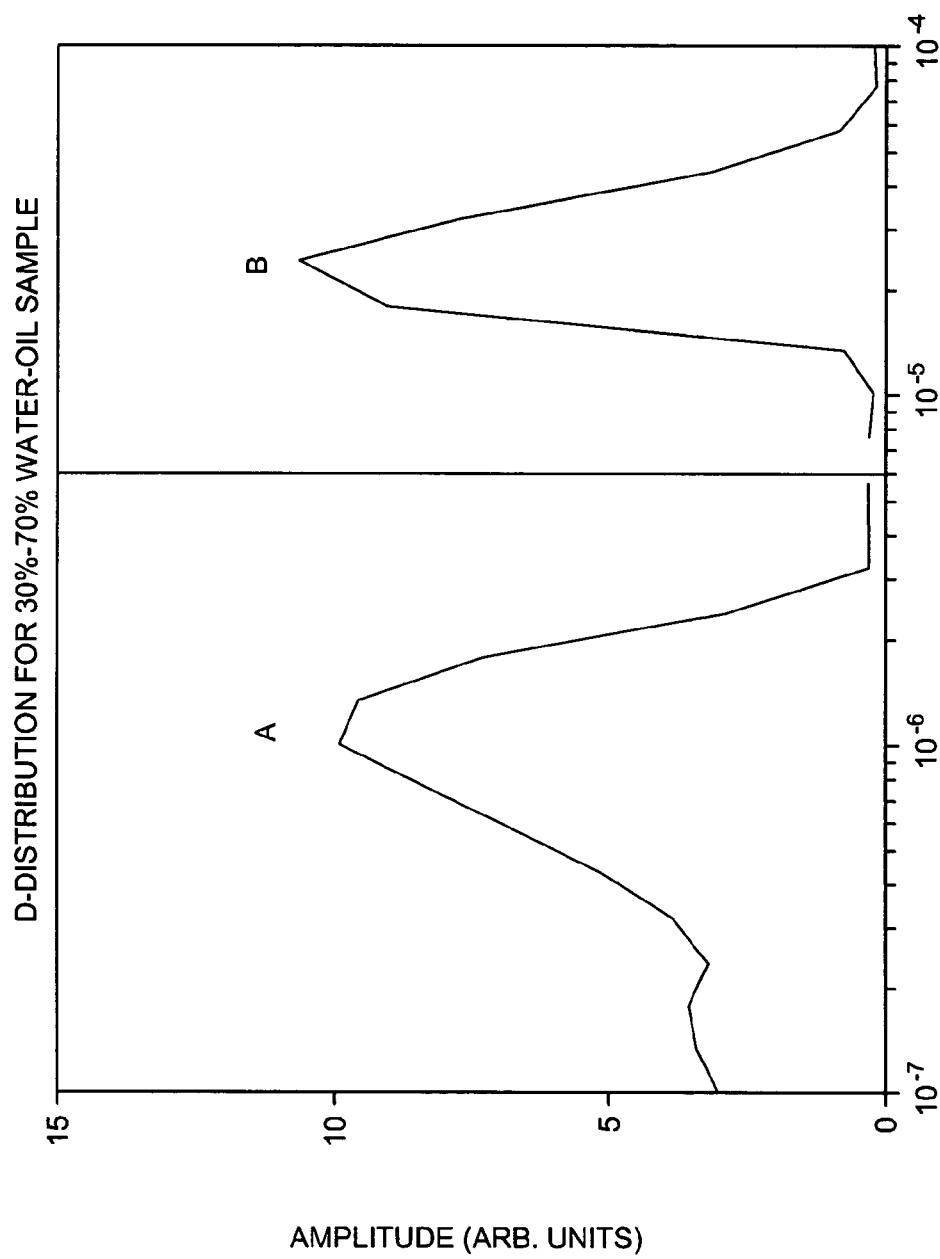
FIG. 8 shows a 1D distribution function extracted from the 2D distribution function shown in FIG. 7 in accordance with one embodiment of the invention.

One-dimensional diffusion distribution functions may similarly be obtained by integrating $f(T_2,D)$ over $T_2$ or by summation of $f_{l,k}$ over the index l. The 1-D diffusion distribution function shown in FIG. 8 was computed from the 2-D distribution function (shown in FIG. 7) by summation of $f_{l,k}$ over the index l. This is equivalent to "projecting" the 2-D plot onto the diffusion axis. Peak A and peak B in FIG. 8 show the 1D distribution functions of diffusion coefficient of the oil peak and the water peak, respectively, in FIG. 7.

The above description illustrate a method of the invention as used in the inversion of a suite of "diffusion encoded" data. The inversion involves a forward model and produces a distribution function that relates the diffusion coefficients of the fluids with the NMR properties (e.g., relaxation times) of the fluids. Individual properties of the fluids can then be extracted from the distribution function. For example, FIG. 8 shows the diffusion coefficients of the fluid components as derived from this approach. The distribution functions and the derived fluid properties (diffusion coefficients and relaxation times) can find many applications in the formation fluid characterization, as illustrated in the following sections.

Reservoir Fluid Properties and Saturations

In many situations of practical interest, the diffusion coefficients of different components in a reservoir fluid are distinct. Generally, gas molecules have the largest diffusion coefficients, followed by water and then oil. Compared with intermediate viscosity oils (viscosity greater than say 5 cp and less than 30 cp), water molecules diffuse about 10 times faster. This can be seen in the plot shown in FIG. 7 for a fluid sample containing water and an intermediate viscosity oil. In FIG. 7, the oil and water signals are well separated in both the diffusion coefficient domain and the relaxation time domain. The $T_2$ separation would be different if the NMR measurements are performed with the fluid in a rock. This is because the surface relaxation from the rock could shorten the $T_2$ relaxation time of the water, leading to potential overlaps of the T2 distributions of water and oils. In FIG. 7, the presence of both oil and water is clearly discernable because the fluid sample is not in a rock. The horizontal line in FIG. 7 marks the water diffusion coefficient, which in this example is about $2.5 \times 10^{-5}$ cm$^2$/s, and the oblique line indicates the relationship between relaxation times and diffusion coefficients for the crude oils, as predicted by the constituent viscosity model (CVM) disclosed in U.S. Pat. No. 6,229,308 B1. The CVM correlates diffusion coefficients and relaxation times of fluid components according to the following equation:

$$D_{o,k} = \lambda \cdot T_{2o,k} f(GOR). \tag{15}$$

where $f(GOR)$ is a known function of gas/oil ratio. $f(GOR)$ is equal to 1 for dead oils (oils without gas) and greater than 1 for live oils. For the dead oil in FIG. 7, a $\lambda$ value of $5.1 \times 10^{-6}$ cm$^2$/s$^2$ was used to construct the oblique line. In a D-T2 plot, the amplitude of the oil signal for most dead crude oils will lie along or close to this reference line. For live oils, the signal amplitude will be shifted to towards the northwest part (upper left) of the plot. In both cases, the slope of the line defining the ridge of the peak of the crude oils in a D-T2 log-log plot should be close to 1 (see e.g., the oblique line in FIG. 7).

Method 1 for Computing Fluid Volumes

The double integral of $f(D,T_2)$ over D and $T_2$ or the double summation of $f_{l,k}$ over both indices l and k is equal to the total signal amplitude or total raw fluid volume ($V_T$) from all fluids in the measurement volume. The raw (i.e., uncorrected for hydrogen index effects) fluid volumes can be corrected for hydrogen index effects as discussed below. In situations like the one depicted in FIG. 7, where the water and oil signals are well separated, it is straightforward to compute the raw oil ($V_o$) and water ($V_w$) volumes. As noted above, the 1-D diffusion distribution ($f(D_k)$) shown in FIG. 8 was computed from the 2-D plot of the diffusion and relaxation time distribution function, $$f(D_k) = \sum_{l=1}^{N} f_{l,k}. \tag{16}$$

Because the oil and water are clearly separated in FIG. 7 and FIG. 8, the raw volume of water ($V_w$) can be computed by summing $f(D_k)$ over those values of $D_k$ that are to the right of the vertical line in the plot in FIG. 8. The raw oil volume ($V_o$) can then be computed from the equation, $$V_o = V_T - V_w, \tag{17}$$

or equivalently by summing the 1-D diffusion distribution function shown over diffusion coefficients to the left of the vertical line in FIG. 8. The water saturation ($S_w$) can be computed from these raw volumes after correcting for hydrogen index effects as shown in Eq. 20. This technique when applied to the 1-D diffusion distribution in FIG. 8 yielded a water saturation of 33.2% that compares favorably with the true saturation of 30%.

The fluid saturations can be computed by correcting the fluid raw volumes for hydrogen index effects. An effective hydrogen index (HI$_{eff}$) may be defined such that, $$\frac{V_T}{HI_{eff}} \equiv \frac{V_w}{HI_w} + \frac{V_0}{HI_0}. \tag{18}$$

HI$_w$ and HI$_o$ are the hydrogen indices of the water and oil, respectively. The hydrogen index of the water (HI$_w$) can be computed from empirical correlations if the salinity of the water is known from resistivity or other measurements. Rearranging Eq. 18, the effective hydrogen index (HI$_{eff}$) can be expressed in terms of the raw fluid volumes and the hydrogen index of the water and oil, $$HI_{eff} = \frac{V_T \cdot HI_w \cdot HI_0}{V_w \cdot HI_0 + V_0 \cdot HI_w}. \tag{19}$$

The water saturation ($S_w$) is by definition the ratio of the hydrogen index corrected volume of water to the corrected total fluid volume, e.g., $$S_w = \frac{V_w \cdot HI_{eff}}{V_T \cdot HI_w} \equiv \frac{V_w \cdot HI_0}{V_w \cdot HI_0 + V_0 \cdot HI_w}. \tag{20}$$

Therefore, water saturation can be computed from the raw volumes computed from the diffusion and relaxation time distribution if the hydrogen indices of the oil and water are known or can be estimated from other measurements. The water saturation provides the "water cut" of the sample drawn into the fluid sampling tool. The oil saturation is simply given by, $$S_0 = 1 - S_w \equiv \frac{V_0 \cdot HI_w}{V_w \cdot HI_0 + V_0 \cdot HI_w}. \qquad (21)$$

Method 2 for Computing Fluid Volumes

The method discussed above for computing raw fluid volumes from plots of diffusion and relaxation time distributions requires that the peaks for the fluid components be separated. In instances of low viscosity oils and water, the diffusion and relaxation time distributions of oils and water can overlap with each other. In this case, it becomes impossible to draw a vertical line like the one shown in FIG. 8. In such cases, a model-based approach may be used. Eq. 15 relates the diffusion coefficient distributions of crude oils to their relaxation time distributions. Consider the discrete set of diffusion and relaxation time amplitudes $f_{l,k}$. There are N diffusion coefficient distributions with logarithmic means denoted by $D_{LM}(l)$, i.e., one for each relaxation time $T_{2,l}$. The amplitudes in the diffusion coefficient distributions correspond to the different values of diffusion coefficients and are the rows in the $f_{l,k}$ matrix. For a sample containing water and oil, the $D_{LM}(l)$ can be related to the fractions of water ($S_w(l)$) with relaxation times $T_{2,l}$ by the equation, $$D_{LM}(l) = D_w^{S_w(l)} \cdot D_o^{1-S_w(l)}. \qquad (22)$$

As shown below, the $D_{LM}(l)$ can be computed from the amplitudes $f_{l,k}$, the diffusion coefficient of water can be determined from the measured temperature of the sample, and the oil diffusion coefficient can be determined using Eq. 15. To compute $D_{LM}(l)$, it is convenient to first compute the quantity, $$m(l) = \sum_{k=1}^{N} \overline{f}_{l,k} \log_e(D_k), \qquad (23)$$

where the $D_k$ are the diffusion coefficients in Eq. 4 and are equally spaced on a logarithmic scale, e.g., $$D_k = D_{min} \cdot \left(\frac{D_{max}}{D_{min}}\right)^{\frac{k-1}{N-1}} \qquad (24)$$

for k=1, 2, ..., N; $D_{min}$ and $D_{max}$ specify the minimum and maximum limits on the diffusion coefficient values used in the computation of the $f_{l,k}$ and, $$\overline{f}_{l,k} = \frac{f_{l,k}}{\sum_{k=1}^{N} f_{l,k}} \equiv \frac{f_{l,k}}{f(T_{2,l})}. \qquad (25)$$

Solving Eq. 22 for the fraction of water with relaxation time $T_{2,l}$ and using Eq. 15 one finds, $$S_w(l) = \frac{\log D_{LM}(l) - \log[\lambda \cdot T_{2,l} \cdot f(GOR)]}{\log D_{H2O} - \log[\lambda \cdot T_{2,l} \cdot f(GOR)]}. \qquad (26)$$

The total (raw) volume of water from all values of $T_{2,l}$ is given by the sum, $$V_w = \sum_{l=1}^{N} S_w(l) \cdot f(T_{2,l}) \equiv \sum_{l=1}^{N} f_w(T_{2,l}), \qquad (27)$$

and the total volume of oil is, $$V_0 = \sum_{l=1}^{N} (1 - S_w(l)) \cdot f(T_{2,l}) \equiv \sum_{l=1}^{N} f_0(T_{2,l}). \qquad (28)$$

$f(T_{2,l})$ in the above equations is the 1-D distribution function (for both oil and water) computed from the 2-D distribution function (as shown in FIG. 7). Note that the functions $f_w(T_{2,l})$ and $f_o(T_{2,l})$ are the 1-D T2 distribution functions for water and oil, respectively. The total water saturation ($S_w$) can be computed from the raw volumes in Eqs. 27–28 using Eq. 20. The partial water saturations in Eq. 26 will sometimes be negative or greater than 1. This can be caused by noise or numerical errors in the diffusion and relaxation time distribution. In applying the above method, partial values that are negative are set to zero and values greater than 1.0 are set equal to 1.0. Eqs. (22)–(28) were used to compute the total water saturation using the 2-D distribution in FIG. 7. A water saturation of 25.3% was computed which compares reasonably well with the true value of 30% that was used in the simulation.

Method 3 for Computing Fluid Volumes

Eqs. 22–28 for computing the fluid volumes represent an approximate and simplified implementation of the NMR fluid characterization method developed by Freedman and described in U.S. Pat. No. 6,229,308 B1 (the '308 patent). This patent discloses a diffusion-based fluid typing method for NMR logging tools that measure fluids in the rock formations surrounding a borehole. A method of the '308 patent uses suites of diffusion-encoded data acquired in the static gradient of the logging tool. As shown below, the Freedman method can be applied to determine the properties of live reservoir fluids that are withdrawn into a fluid sampling module using suites of pulsed field gradient data.

Consider a sample of reservoir fluid that has been withdrawn into a fluid sampling tool flowline or diverted into a special sample chamber where pulsed field gradient and other NMR measurements can be performed while the flow is stopped (i.e., on the stationary fluid). The samples may contain oil (o), water (w), and/or gas (g). A multi-fluid forward model for the transverse magnetization measured by a suite of PFG-CPMG measurements made on such a sample is as follows:

$$M(t) = f_w \cdot \exp\left(-\frac{t}{T_{2,w}}\right) \cdot \left(1 - \exp\left(-\frac{W}{T_{1,w}}\right)\right) \cdot \quad (29)$$
$$\exp(-(\gamma \cdot g \cdot \delta)^2 \cdot D_w(T) \cdot (\Delta - \delta/3)) +$$
$$\int f_0(T_2) \cdot \exp\left(-\frac{t}{T_2}\right) \cdot \left(1 - \exp\left(-\frac{W}{\xi_0 \cdot T_2}\right)\right) \cdot$$
$$\exp(-(\gamma \cdot g \cdot \delta)^2 \cdot (\lambda \cdot T_2 \cdot f(GOR)) \cdot (\Delta - \delta/3)) dT_2 +$$
$$f_g \cdot \exp\left(-\frac{t}{T_{2,g}}\right) \cdot \left(1 - \exp\left(-\frac{W}{T_{1,g}}\right)\right) \cdot$$
$$\exp(-(\gamma \cdot g \cdot \delta)^2 \cdot D_g(P,T) \cdot (\Delta - \delta/3)).$$

It should be understood that equations similar to Eq. 29 can be applied to suites of SEPFG-CPMG data. The first term in Eq. 29 is the contribution to the measured transverse magnetization from water in the fluid sample. The amplitude of the water signal is $f_w$. Note that the spin-spin decay of the transverse magnetization from the bulk water signal is a single exponential with relaxation time $T_{2,w}$. This is very different from the spin-spin decay of water measured in porous rocks, for which the surface relaxation produces a distribution of relaxation times. Similarly, the longitudinal relaxation time for bulk water is a single exponential with relaxation time $T_{1,w}$. Also, note that for bulk water $T_{2,w}=T_{1,w}$. However, this is not true for water in porous rocks. The diffusion coefficient $D_w(T)$ of water is a known function of the sample temperature (T) that can be measured by a temperature sensor.

The second term in Eq. 29 is the contribution to the measured transverse magnetization from oils in the fluid sample. Crude oils have a distribution of spin-spin relaxation times and, therefore, the oil contribution involves an integral over the oil relaxation time distribution $f_o(T_2)$. The parameter $\xi_0$ in the polarization function is the T1/T2 ratio for the crude oil. The T1/T2 ratio can differ substantially from 1 and is generally found to increase with increasing measurement frequency and oil viscosity. The fluid characterization method in U.S. Pat. No. 6,229,308 B1 was used to account for the distribution of diffusion coefficients in crude oils, i.e., $D_o(T)$ in the second term of Eq. 29 was replaced using Eq. 15. If the fluid sampling is done in a well drilled with oil-based mud, then the oil term may describe a mixture of native crude oil and oil-based mud filtrate, depending on the level of sample contamination.

The last term in Eq. 29 is the contribution to the measured transverse magnetization from gas in the fluid sample. For reservoirs containing live oils, the fluid pressure during sampling is usually above the bubble point so that a single phase (oil) is pumped into the sampling tool. However, there can be cases where oil and gas phases are both present in the sample. The amplitude of the gas signal is $f_g$. The gas signal decays with a single spin-spin relaxation time $T_{2,g}(P,T)$ that may be a measured or computed function of temperature and pressure. Likewise, gas relaxes with a single longitudinal relaxation time $T_{1,g}(P,T) \approx T_{2,g}(P,T)$ and has a single diffusion coefficient $D_g(P,T)$ that may be a measured or computed function of temperature and pressure.

The model-dependent transverse magnetization in Eq. 29 can be inverted using suites of data similar to those used to invert the model-independent transverse magnetization in Eqs. 1 and 3. The model parameters determined by inversion of the forward model in Eq. 29 are the water and gas amplitudes, $f_w$ and $f_g$, the T1/T2 ratio, $\xi_o$, of the oil, and the distribution $f_o(T_2)$ of spin-spin relaxation times of the crude oil. The amplitudes may then be used to compute the fluid volumes and saturations of the gas, water, and oil. The model parameters required for the inversion are $T_{2,w}$, $D_w(T)$, $\lambda$, GOR, and $T_{2,g}$. Except for the GOR, these parameters can be estimated from empirical correlations if the temperature and pressure of the sample are measured by sensors in the sampling tool (Kleinberg and Vinegar, 1996, "*NMR Properties of Reservoir Fluids*" in *The Log Analyst*, vol. 37, no. 6, p. 20–32.; Freedman et al., 2001, *"A New NMR Method of Fluid Characterization in Reservoir Rocks: Experimental Confirmation and Simulation Results"* in SPE Journal, vol. 6, no. 4, p. 452–464.). The GOR can be obtained from other fluid sampling tool measurements, e.g., from a near infrared absorption spectrum of the fluid that can be measured with a suitable tool, such as the Optical Fluid Analyzer Tool sold by Schlumberger Technology Corp. (see U.S. Pat. No. 6,350,986 B1 issued to Mullins et al.).

Accurate values for some of these parameters can be obtained by determining them from a suite of NMR measurements, for example, by inversion of the model-independent equations for the transverse magnetization (i.e., Eqs. 1–3) to compute a 2-D or 3-D diffusion and relaxation time distribution functions, as described above. A plot like the one in FIG. 7 of a model-independent distribution function contains the signals from all of the fluids that are present. For example, the sample in FIG. 7 contains oil and water. It is apparent from the plot that the peak at $T_{2,w} \cong 5s$, $D'' \cong 2.5 \times 10^{-5}$ cm$^2$/s can be ascribed to water, and from the distribution function or its plot, it can be determined that $\lambda \cong 5.1 \times 10^{-6}$ cm$^2$/s$^2$. Therefore, more accurate fluid volumes and saturations can be determined using Eq. 29 by first determining the model-independent diffusion and relaxation time distribution function to provide more accurate input parameters for Eq. 29. Also, because the model-independent distribution function is useful in identifying the fluids that are present, one can determine which terms in Eq. 29 must be included and which, if any, can be dropped.

Inversion of Eq. 29 can be performed using the "window processing" method described above or by using any other suitable method known in the art for fitting a suite of pulse field gradient measurements to the Eq. 29. Such methods, for example, include least squares, maximum entropy, or other minimum error methods. After the inversion, the fluid volumes and saturations may be readily determined. For example, the fluid saturations may be determined according to the following equations:

$$S_w = \frac{f_w}{f_w + \frac{HI_w \cdot f_g}{HI_g} + \frac{HI_w \cdot \sum_{i=1}^{N} f_0(T_{2,i})}{HI_0}}, \quad (30)$$

$$S_g = \frac{f_g}{f_g + \frac{HI_g \cdot f_w}{HI_w} + \frac{HI_g \cdot \sum_{i=1}^{N} f_0(T_{2,i})}{HI_0}}, \text{ and} \quad (31)$$

$$S_0 = 1 - S_w - S_g.$$

Computation of Viscosity, GOR, Oil Composition, and Formation Temperature

In the sections above, three methods for computing fluid saturations and volumes and a method for determining the T1/T2 ratio of the oil from pulsed field gradient measurements are described. The oil viscosity, GOR, oil compositions, and formation temperature can also be computed from these measurements. The following sections describe exemplary methods for calculating these parameters.

Viscosity

The oil viscosity can be computed from any known correlations that relate viscosity to relaxation times. For example, the logarithmic mean, $T_{2,LM}$, of the 1-D relaxation time distribution may be related to oil viscosity ($\eta_o$) and GOR by the empirically determined equation disclosed in Freedman et al., 2001, *"A New NMR Method of Fluid Characterization in Reservoir Rocks: Experimental Confirmation and Simulation Results"* in SPE Journal, vol. 6, no. 4, p. 452–464.)

$$\eta_0 = \frac{a \cdot T}{T_{2,LM} \cdot f(GOR)}, \quad (32)$$

where T is temperature in degrees Kelvin, $f(GOR) \geq 1$ is an empirically determined function (Lo, et al., "Mixing Rules and Correlations of NMR Relaxation Time With Viscosity, Diffusivity, and Gas/Oil Ratio of Methane/Hydrocarbon Mixtures" in *SPE Journal*, vol. 7, no. 1, p. 24–34, March 2002) and the parameter $a \cong 0.004$–$0.009$ s·cp·K$^{-1}$, depending on the oils (Freedmanand Heaton, "Fluid Characterization Using Nuclear Magnetic Resonance Logging in *Petrophysics*, vol. 45, no. 3, p. 241–251, 2004). This variation means that viscosity can only be estimated to within about a factor of two. In Eq. 32, the viscosity is in units of centipoise (cp) and the logarithmic mean relaxation time is in seconds.

In addition to Eq. 32, other functions that relate $T_{1,LM}$ to viscosity can also be used to calculate viscosities. For example, the logarithmic mean, $D_{LM}$, of the 1-D diffusion distribution can also be used to compute oil viscosity, e.g., $$\eta_o = \frac{b \cdot T}{D_{LM}}. \quad (33)$$

The parameter, $b=5.05 \times 10^{-8}$ cm$^2$·cp·K$^{-1}$, in Eq. 33 is an empirically determined constant that is valid for many crude oils. It should be understood that Eqs. 32 and 33 are based on correlations determined using low field NMR (e.g., proton Larmor frequencies from 1 to 4 MHz) and that the parameters (e.g., a and b) in these equations may need to be changed for measurements made at higher frequency.

Gas/Oil Ratio

After 1-D distributions are computed for both diffusion and relaxation times, the function $f(GOR)$ (and therefore the GOR) can be estimated from the equation, $$f(GOR) = \frac{D_{LM}}{T_{2,LM} \cdot \lambda}, \quad (34)$$

where the value of $\lambda$ is determined either from a 2-D diffusion and relaxation time distribution or a nominal value, $\lambda \approx 5.1 \times 10^{-6}$ cm$^2$/s$^2$, which has been found to be valid for many oils, can be used.

Oil Composition

U.S. Patent Application Publication No. 2003/0128032 A1 filed by Heaton et al. and assigned to the assignee of the present invention discloses how to compute the molecular composition of crude oils from measured relaxation time and diffusion distribution functions. This application is incorporated in its entirety by reference.

Formation Temperature

The fluid sample temperature is needed to compute oil viscosity from Eqs. 32–33. If the fluid sample withdrawn from the formation contains water, then the temperature-dependent diffusion coefficient of the water ($D_w(T)$) is determined from the 2-D distribution function like the one shown in FIG. 7. Because $D_w(T)$ is a monotonically increasing function of water temperature (see e.g., Kleinberg and Vinegar, *"NMR Properties of Reservoir Fluids"* The Log Analyst, p. 25, November–December 1996), the water temperature (T) of the sample can be determined from the measured water diffusion coefficient. Because the water is in thermal equilibrium with any oil or gas in the fluid sample, the water temperature is also the temperature of the entire fluid sample. The water temperature may serve as a lower bound of the formation temperature because some cooling of the fluid sample may have occurred after it is withdrawn from the formation.

Computation of Diffusion and Relaxation Time Distributions for Spatially Varying Gradient In the foregoing analysis it was assumed that the pulsed field gradient g is constant over the volume of the sample. In practice, this condition may not be simple to achieve and there can be a distribution of gradients described by a function F(g). In this case, the equations for the transverse magnetization (e.g., see Eqs. 1–4) may be modified to include an integration of the gradient distribution. For example, Eq. 3 may be re-written as, $$M(g;t) = \int \int f(D, T_2) \cdot \exp(-t/T_2) \cdot \exp(-(\gamma \cdot g \cdot \delta)^2 D(\Delta - \delta/3)) \, dD dT_2, \quad (35)$$

where the dependence of the magnetization on the gradient g is shown explicitly. Then, if there is a distribution of gradients, Eq. 3 may be replaced by, $$M(t) = \int F(g) \cdot M(g, t) dg \cong \sum_i F_i M(g_i, t), \quad (36)$$

where the integral has been replaced by a discrete sum of the distribution. The inversion of Eq. 36 may be performed as discussed above for the case of a constant gradient.

Advantages of the invention may include one or more of the following. The use of pulsed field gradients to encode diffusion information in the absence of appreciable static gradients can provide many advantages over the prior art well logging methods that use the gradient in the static magnetic field of the NMR magnet (see e.g., "Experimental Pulse NMR—A Nuts and Bolts Approach," Fukushima and Roeder, Perseus Publishing, Boulder, Colo., 1986). One of the advantages of using the pulsed field gradient methods is that the gradient is turned-off during the echo acquisition. This results in wider and more easily detectable echoes than does a static field gradient, which tends to produce narrower echoes. Also, when a static gradient is on during the RF pulses used to rotate the magnetization, only spins in a shell with thickness of order $B_1/G$ are in resonance, where $B_1$ is the magnitude of the RF field and G is the magnitude of the static field gradient. At low RF power (e.g., small $B_1$ amplitudes) or for high static gradients the shell thickness, and therefore the resonated volume of the sample, can be less than desired. By contrast, with the pulsed field gradient method, the whole sample volume can be resonated, resulting in better signal-to-noise ratios. Also, the gradient pulses can be used to encode diffusion information and then turned off so that T2 relaxation time data can be acquired in the absence of a magnetic field gradient. This has the advantage that fluids with long T2 values can be measured more accurately because there is no loss of signal amplitude caused by molecular diffusion in a magnetic field gradient.

While this invention has been demonstrated using limited embodiments, those skilled in the art, having benefit of this disclosure, will appreciate that other methods can be devised without departing from the scope of the invention as disclosed herein. Accordingly, the scope of the invention should be limited only by the attached claims.

What is claimed is:

1. A method for determining a formation fluid property, comprising:
    acquiring a suite of nuclear magnetic resonance (NMR) measurements of a fluid sample using a pulse sequence that includes pulsed field gradient pulses for encoding diffusion information, wherein each NMR measurement in the suite is acquired with a different value in a parameter in the pulsed field gradient pulses for producing a different diffusion effect, wherein the acquiring is performed in a formation fluid sampling tool in a borehole;
    inverting the suite of NMR measurements to produce a distribution function that relates diffusion properties of the fluid sample with an NMR property of the fluid sample; and
    determining the formation fluid property from the distribution function.

2. The method of claim 1, wherein a spin-echo that follows the pulsed field gradient pulses for each measurement in the suite is repeatedly re-focused by 180-degree pulses that produce a train of spin-echo signals in order to provide information on spin-spin relaxation times of the fluid sample.

3. The method of claim 1, wherein the each NMR measurement is acquired with a different wait time in order to provide information on longitudinal relaxation times of the fluid sample.

4. The method of claim 1, wherein the pulsed field gradient pulses comprises a stimulated echo pulsed field gradient pulse sequence.

5. The method of claim 1, wherein the parameter in the pulsed field gradient pulses is one selected from a gradient strength (g), a duration for the pulsed field gradient pulses ($\delta$), and a delay time between the gradient pulses ($\Delta$).

6. The method of claim 1, wherein the acquiring is performed in the presence of a substantially homogeneous static magnetic field.

7. The method of claim 1, wherein the inverting uses a model that relates the magnetization relaxation with diffusion of the fluid sample.

8. The method of claim 1, wherein the distribution function is a two-dimensional distribution function or a three-dimensional distribution function.

9. The method of claim 1, wherein the NMR property is a spin-spin relaxation time.

10. The method of claim 1, wherein the formation fluid property is one selected from a diffusion coefficient, a viscosity, a gas-oil ratio, an oil molecular composition, a water saturation, and an oil saturation.

11. An NMR sensor for a downhole tool, comprising:
    a permanent magnet capable of generating a substantially homogeneous magnetic field across a sample chamber;
    a radiofrequency antenna surrounding the sample chamber, wherein the radiofrequency antenna is configured to generate oscillating magnetic fields that have magnetic moments substantially orthogonal to a direction of the substantially homogeneous magnetic field generated by the permanent magnet; and
    at least one coil connected to a control unit, wherein the at least one coil and the control unit are configured to generate pulsed magnetic field gradient across the sample chamber in a controlled manner such that the pulsed magnetic field gradient has a selected strength and a predetermined duration.

12. The NMR sensor of claim 11, further comprising a casing for protecting the permanent magnet, the radiofrequency antenna, the sample chamber, the at least one coil and the control unit.

13. The NMR sensor of claim 12, wherein the casing is made of a magnetically permeable material.

14. A downhole tool, comprising:
    a tool body configured to move in a borehole; and
    an NMR module disposed in the tool body, wherein the NMR module comprises:
        a permanent magnet capable of generating a substantially homogeneous magnetic field across a sample chamber;
        a radiofrequency antenna surrounding the sample chamber, wherein the radiofrequency antenna is configured to generate oscillating magnetic fields that have magnetic moments substantially orthogonal to a direction of the substantially homogeneous magnetic field generated by the permanent magnet; and
        at least one coil connected to a control unit, wherein the at least one coil and the control unit are configured to generate pulsed magnetic field gradient across the sample chamber in a controlled manner such that the pulsed magnetic field gradient has a selected strength and a predetermined duration.

15. The downhole tool of claim 14, further comprising a casing for protecting the permanent magnet, the radiofrequency antenna, the sample chamber, the at least one coil and the control unit.

16. The downhole tool of claim 15, wherein the casing is made of a magnetically permeable material.

17. The method of claim 1, further comprising:
    acquiring the formation fluid sample for NMR measurements within the formation fluid sampling tool.

* * * * *